United States Patent
Lee et al.

(10) Patent No.: US 12,106,474 B2
(45) Date of Patent: Oct. 1, 2024

(54) METHOD OF DETERMINING A DISTRIBUTION OF STEM CELLS IN A CELL IMAGE, ELECTRONIC DEVICE, AND STORAGE MEDIUM

(71) Applicant: HON HAI PRECISION INDUSTRY CO., LTD., New Taipei (TW)

(72) Inventors: Wan-Jhen Lee, New Taipei (TW); Chin-Pin Kuo, New Taipei (TW); Chih-Te Lu, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 472 days.

(21) Appl. No.: 17/526,280

(22) Filed: Nov. 15, 2021

(65) Prior Publication Data
US 2022/0207724 A1 Jun. 30, 2022

(30) Foreign Application Priority Data
Dec. 24, 2020 (CN) .......................... 202011553990.3

(51) Int. Cl.
*G06T 7/00* (2017.01)
*C12M 1/34* (2006.01)

(52) U.S. Cl.
CPC ........... *G06T 7/0012* (2013.01); *C12M 41/36* (2013.01); *C12M 41/46* (2013.01);
(Continued)

(58) Field of Classification Search
CPC ................. C12M 41/36; C12M 41/46; G06T 2207/10056; G06T 2207/20084;
(Continued)

(56) References Cited

U.S. PATENT DOCUMENTS

| | | | |
|---|---|---|---|
| 2010/0184093 A1* | 7/2010 | Donovan ............... | G16B 25/00 435/287.1 |
| 2013/0183707 A1* | 7/2013 | Mangoubi .............. | G16B 40/20 702/19 |

(Continued)

FOREIGN PATENT DOCUMENTS

| CN | 111126329 | 5/2020 |
|---|---|---|
| TW | 710762 | 11/2020 |

OTHER PUBLICATIONS

Reema A. Khorshed et al., "Automated Identification and Localization of Hematopoietic Stem Cells in 3D Intravital Microscopy Data," Jul. 14, 2015, Stem Cell Reports, vol. 5, Jul. 14, 2015, pp. 139-149.*

(Continued)

*Primary Examiner* — Omar S Ismail
(74) *Attorney, Agent, or Firm* — ScienBiziP, P.C.

(57) ABSTRACT

A method of determining a distribution of stem cells in a cell image, an electronic device and a storage medium are disclosed. The method acquires a cell image and segments the cell image and obtaining a plurality of sub-images. The plurality of sub-images is inputted into a stem cell detection model to detect to obtain a number of stem cells in each sub-image. A position of each sub-image in the cell image is determined. A distribution of the stem cells in the cell image is output, according to the number of stem cells in each sub-image and the position of each sub-image in the cell image. The present disclosure an accuracy of the distribution of stem cells in the cell image.

17 Claims, 2 Drawing Sheets

(52) U.S. Cl.
CPC .............. *G06T 2207/10056* (2013.01); *G06T 2207/20112* (2013.01); *G06T 2207/30024* (2013.01)

(58) Field of Classification Search
CPC . G06T 2207/20112; G06T 2207/30024; G06T 7/0012; G06V 20/695
See application file for complete search history.

(56) References Cited

U.S. PATENT DOCUMENTS

| | | | |
|---|---|---|---|
| 2015/0153326 A1* | 6/2015 | Kogel | G01N 15/08 435/5 |
| 2016/0055292 A1* | 2/2016 | White | G06T 11/206 702/19 |
| 2019/0256817 A1* | 8/2019 | Gebhart | G01N 21/6428 |
| 2019/0384047 A1* | 12/2019 | Johnson | G06N 3/045 |
| 2021/0095331 A1* | 4/2021 | Fan | G01N 33/56966 |
| 2021/0133981 A1* | 5/2021 | Chen | G06T 7/11 |

OTHER PUBLICATIONS

Robert Sheng Xu, "An Information Tracking Approach to the Segmentation of Prostates in Ultrasound Imaging," A thesis presented to the University of Waterloo, Canada, 2010, pp. 45-70.*
Sotiris Dimopoulos et al, "Accurate cell segmentation in microscopy images using membrane patterns," Apr. 24, 2014, Bioinformatics, vol. 30, No. 18, 2014, pp. 2644-2648.*

* cited by examiner

METHOD OF DETERMINING A DISTRIBUTION OF STEM CELLS IN A CELL IMAGE, ELECTRONIC DEVICE, AND STORAGE MEDIUM

FIELD

The present disclosure relates to a technical field of image detection, specifically a method of determining a distribution of stem cells in a cell image, an electronic device and a storage medium.

BACKGROUND

In addition to stem cells, there are other impurities or other cells appearing in a cell image, and the size and shape of stem cells are inconsistent or even overlap each other, resulting in low accuracy of determining the distribution.

Accurately determining a distribution of stem cells is problematic.

DETAILED DESCRIPTION

The accompanying drawings combined with the detailed description illustrate the embodiments of the present disclosure hereinafter. It is noted that embodiments of the present disclosure and features of the embodiments can be combined, when there is no conflict.

Various details are described in the following descriptions for a better understanding of the present disclosure, however, the present disclosure may also be implemented in other ways other than those described herein. The scope of the present disclosure is not to be limited by the specific embodiments disclosed below.

Unless defined otherwise, all technical and scientific terms used herein have the same meaning as commonly understood by one of ordinary skill in the art to which the present disclosure belongs. The terms used herein in the present disclosure are only for the purpose of describing specific embodiments and are not intended to limit the present disclosure.

Optionally, the method of determining a distribution of stein cells in a cell image of the present disclosure is applied to one or more electronic devices. The electronic device includes hardware such as, but not limited to, a microprocessor and an Application Specific Integrated Circuit (ASIC), Field-Programmable Gate Array (FPGA), Digital Signal Processor (DSP), embedded devices, etc.

The electronic device may be a device such as a desktop computer, a notebook, a palmtop computer, or a cloud server. The electronic device can interact with users through a keyboard, a mouse, a remote control, a touch panel, or a voice control device.

Figure 1:
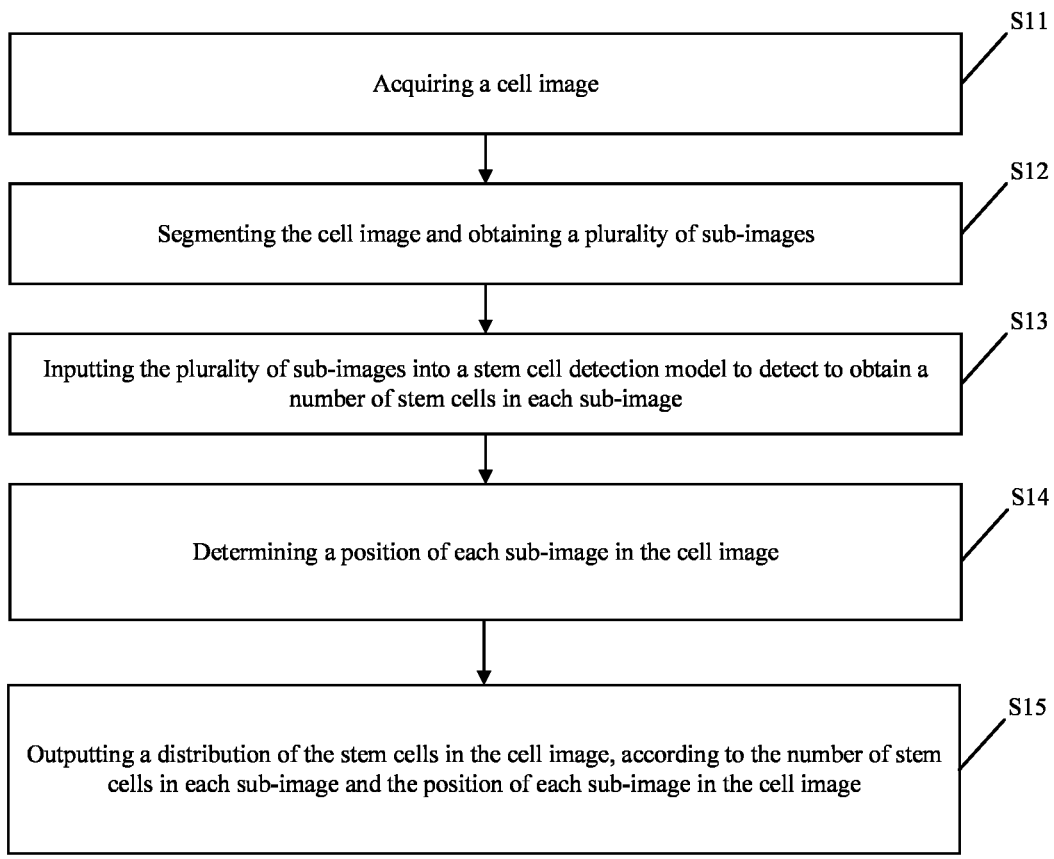
FIG. 1 shows a flowchart of a method of determining a distribution of stem cells in a cell image provided in an embodiment of the present disclosure.

FIG. 1 is a flowchart of a method of determining a distribution of stem cells in a cell image in an embodiment of the present disclosure. According to different needs, the order of the steps in the flowchart can be changed, and some can be omitted.

In block S11, acquiring a cell image.

The cell image refers to an image of cells that needs to be analyzed regarding a distribution of stem cells shown in the cell image. The cell image may include portrayals of, but is not limited to, stem cells, other cells, and impurities.

In some embodiments, before acquiring the cell image, the method also includes training a stem cell detection model. The stem cell detection model is used to detect several stem cells in a cell image.

In some embodiments, a process of training the stem cell detection model includes acquiring a plurality of stem cell sample images; extracting features of each stem cell sample image through a residual convolutional network; generating a plurality of first feature maps through a feature pyramid network, according to the extracted features of each stem cell sample; generating a plurality of candidate feature maps through a region candidate network, according to the plurality of first feature maps; screening the plurality of candidate feature maps according to a preset intersection ratio threshold to obtain a plurality of target feature maps; inputting each first feature map and the corresponding target feature map to a region of interest pooling layer and obtaining a plurality of second feature maps; performing a regression training on the plurality of second feature maps and a number of stem cells in each second feature map and obtaining the stem cell detection model.

The plurality of stem cell sample images is pre-collected as a data set for training the stem cell detection model. These stem cell sample images include cell images with different densities of stem cells.

In block S12, segmenting the cell image and obtaining a plurality of sub-images.

The cell image can be a high-resolution digital image acquired by scanning and recording with a fully automatic microscope or an optical magnification system, and then a computer is used to automatically perform high-precision multi-field seamless stitching and processing on the acquired high-resolution digital image to obtain high-quality visualization data for application in various fields of pathology.

The cell image can be segmented to obtain a plurality of sub-images, thus the cell image is never too large to use in the stem cell detection model. At the same time, parallel processing of the plurality of sub-images increases a processing speed.

In some embodiments, after segmenting the cell image and obtaining a plurality of sub-images, the method further includes normalizing each sub-image to obtain a plurality of normalized images and performing gamma correction on each normalized image to obtain a plurality of corrected images.

For each sub-image, pixels of the sub-image can be normalized by a normalization algorithm to obtain a normalized image. For each normalized image, gamma correction can be performed on the normalized image to obtain a corrected image.

Normalization refers to the normalization of the RGB (Red Green Blue) value of the pixels of an image. By normalizing the RGB color space of the sub-image, influence of light on the sub-image is eliminated.

Gamma correction edits the gamma curve of an image to adjust the non-linear tone of the image, so that a ratio between dark parts and light parts in the image signal is increased, thereby improving the image contrast effect.

The cell image will be contaminated by random signals (also known as noise) of different intensities during a process of the acquisition, and this will have unpredictable effects on subsequent image analysis and processing. Therefore, the cell image is normalized, and gamma corrected, these reduce the influence of noise, thereby improving an accuracy of the stem cell detection model to detect the cell image.

In block S13, inputting the plurality of sub-images into a stem cell detection model to detect to obtain a number of stem cells in each sub-image.

The plurality of sub-images is input into the stem cell detection model to obtain the number of stem cells in each of the plurality of sub-images. An accuracy of the number of stem cells detected by the stem cell detection model is relatively high. In other embodiments, a plurality of threads can be created, one stein cell detection model is arranged in each thread, so the number of the stem cell detection models is equal to the number of the plurality of threads. One stem cell detection model is used to detect one sub-image. In this way, the sub-images can be detected in parallel, thereby improving an efficiency of detecting the number of stein cells in the cell image.

In some embodiments, when each sub-image is normalized and corrected, wherein inputting the plurality of sub-images into a stem cell detection model to detect to obtain a number of stem cells in each sub-image includes inputting each corrected image into the stem cell detection model to detect to obtain a number of stem cells in the corresponding sub-image.

When one corrected image is inputted into the stem cell detection model, the stem cell detection model detects a number of stem cells in the one corrected image. One corrected image is corresponding to one sub-image. The number of stem cells in the corrected image is the number of stem cells shown in the corresponding sub-image.

In some embodiments, after inputting the plurality of sub-images into the stem cell detection model, the method further includes determining whether the number of stem cells in each sub-image is greater than a preset second threshold; when it is determined that the number of stem cells in any one sub-image is greater than the preset second threshold, generating an alarm and sending the alarm to a preset terminal device.

For each sub-image, it is determined whether the number of stein cells in the sub-image is greater than the preset second threshold. If the number of stem cells in any one sub-image is less than or equal to the preset second threshold, it indicates that the number of stem cells in the sub-image is normal. If the number of stem cells in any one sub-image is greater than the preset second threshold, this shows that there are too many stem cells in the sub-image, and then an alarm is generated to draw the attention of staff.

In block S14, determining a position of each sub-image in the cell image.

The position of each sub-image in the cell image is determined. The position of the sub-image in the cell image can be represented by pre-set characters. For example, in an order from left to right and from top to bottom, like a subscript of a two-dimensional array. A numeric value "11" represents a position of a sub-image in a first row and a first column in the cell image. A numeric value "12" represents a position of a sub-image in a first row and a second column in the cell image. Numeric values "21", 22, and 23 indicate the positions of three adjacent sub-images, from left to right, in a second row in the cell image.

In block S15, outputting a distribution of the stem cells in the cell image, according to the number of stem cells in each sub-image and the position of each sub-image in the cell image.

The distribution of the stem cells in the cell image represents a number of stem cells at each position in the cell image.

In some embodiments, after outputting a distribution of the stein cells in the cell image, the method further includes receiving an instruction to analyze for stem cells in a designated area in the cell image and acquiring a target sub-image corresponding to the designated area from the plurality of sub-images. The number of stem cells in the target sub-image is determined as a target number of stem cells in the designated area; and whether the target number is determined to be greater than a preset first threshold. Information that the stem cells are not aggregated in the designated area in the cell image is displayed, when the target number is less than or equal to the preset first threshold.

In the above embodiment, when the target number is less than or equal to the preset first threshold, it indicates that there is no accumulation of stein cells in the designated area in the cell image.

In other embodiments, when it is determined that the target number is less than or equal to the preset first threshold, this information, but no other information, may be displayed on the cell image.

In some embodiments, when the target number is greater than the preset first threshold, the method further includes displaying information that the stein cells are aggregated in the designated area in the cell image.

In the above embodiment, when the target number is greater than the preset first threshold, it indicates that there is accumulation of stem cells in the designated area in the cell image. When it is determined that there is accumulation of stem cells in the designated area in the cell image, the information that the stem cells are aggregated can be displayed in the designated area in the cell image, it may be displayed in a form of text on the designated area in the image.

By displaying information that the stem cells are aggregated in the designated area in the cell image, assessing the number of stem cells in certain areas in the image can be done intuitively.

In some embodiments, after outputting a distribution of the stein cells in the cell image and in response to an instruction for calculating a total number of stem cells in the cell image, the method further includes calculating the number of stem cells in each sub-image and obtaining a total number of stem cells in the cell image and outputting the total number of stem cells in the cell image.

The total number of stem cells in the cell image can be obtained by adding up the number of stem cells in all the sub-images.

In the method of determining a distribution of stem cells in a cell image provided by the embodiments of the present disclosure, a cell image is segmented into a plurality of smaller sub-images, and the smaller sub-images are analyzed in parallel through a stem cell detection model to obtain the number of stein cells in each sub-image, thereby obtaining the number of stem cells in the cell image. According to the number of stem cells in each sub-image and the position of each sub-image in the cell image, the distribution of stem cells in the cell image can be determined. The efficiency of determining the distribution of stem cells in the cell image is improved, and at the same time, the accuracy is also improved.

Figure 2:
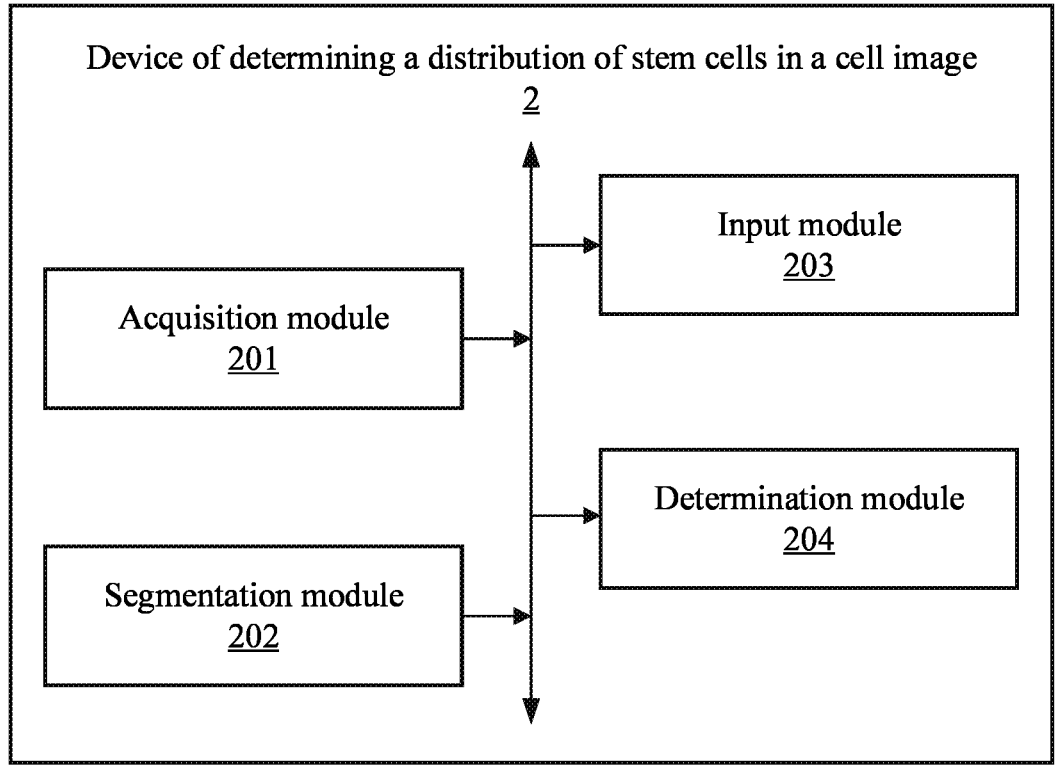
FIG. 2 shows a schematic structural diagram of a device of determining a distribution of stem cells in a cell image provided in an embodiment of the present disclosure.

FIG. 2 shows a schematic structural diagram of a device of determining a distribution of stem cells in a cell image provided in the embodiment of the present disclosure.

In some embodiments, the device of determining a distribution of stem cells in a cell image 2 runs in an electronic device. The device of determining a distribution of stem cells in a cell image 2 can include a plurality of function modules consisting of program code segments. The program code of each program code segments in the device of determining a distribution of stein cells in a cell image 2 can be stored in a memory and executed by at least one processor to perform functions for determining a distribution of stem cells in a cell image (described in detail in FIG. 2).

As shown in FIG. 2, the device determining a distribution of stem cells in a cell image 2 can include: an acquisition module 201, a segmentation module 202, an input module 203, and a determination module 204. A module as referred to in the present disclosure refers to a series of computer-readable instruction segments that can be executed by at least one processor and that are capable of performing fixed functions, which are stored in a memory. In some embodiment, the functions of each module will be detailed.

The above-mentioned integrated unit implemented in a form of software functional modules can be stored in a non-transitory readable storage medium. The above software function modules are stored in a storage medium and includes several instructions for causing an electronic device (which can be a personal computer, a dual-screen device, or a network device) or a processor to execute the method described in various embodiments in the present disclosure.

The acquisition module 201 acquires a cell image.

The cell image refers to an image of cells that needs to be analyzed regarding a distribution of stem cells shown in the cell image. The cell image may include portrayals of, but is not limited to, stem cells, other cells, and impurities.

In some embodiments, before acquiring the cell image, the device also includes training a stem cell detection model. The stem cell detection model is used to detect several stem cells in a cell image.

In some embodiments, the acquisition module 201 acquires a plurality of stem cell sample images; an extraction module extracts features of each stem cell sample image through a residual convolutional network; a generation module generates a plurality of first feature maps through a feature pyramid network, according to the extracted features of each stem cell sample; and generates a plurality of candidate feature maps through a region candidate network, according to the plurality of first feature maps; a selection module screens the plurality of candidate feature maps according to a preset intersection ratio threshold to obtain a plurality of target feature maps; the input module 203 inputs each first feature map and the corresponding target feature map to a region of interest pooling layer and obtains a plurality of second feature maps; a regression module performs a regression training on the plurality of second feature maps and a number of stem cells in each second feature map and obtains the stem cell detection model.

The plurality of stem cell sample images is pre-collected as a data set for training the stem cell detection model. These stem cell sample images include cell images with different densities of stem cells.

The segmentation module 202 segments the cell image and obtains a plurality of sub-images.

The cell image can be a high-resolution digital image acquired by scanning and recording with a fully automatic microscope or an optical magnification system, and then a computer is used to automatically perform high-precision multi-field seamless stitching and processing on the acquired high-resolution digital image to obtain high-quality visualization data for application in various fields of pathology.

The cell image can be segmented to obtain a plurality of sub-images; thus the cell image is never too large to use in the stem cell detection model. At the same time, parallel processing of the plurality of sub-images increases a processing speed.

In some embodiments, after segmenting the cell image and obtaining a plurality of sub-images, the device further includes a processing module and a correction module. The processing module configured to normalize each sub-image to obtain a plurality of normalized images and the correction module configured to perform gamma correction on each normalized image to obtain a plurality of corrected images.

For each sub-image, pixels of the sub-image can be normalized by a normalization algorithm to obtain a normalized image. For each normalized image, gamma correction can be performed on the normalized image to obtain a corrected image.

Normalization refers to the normalization of the RGB (Red Green Blue) value of the pixels of an image. By normalizing the RGB color space of the sub-image, influence of light on the sub-image is eliminated.

Gamma correction edits the gamma curve of an image to adjust the non-linear tone of the image, so that a ratio between dark parts and light parts in the image signal is increased, thereby improving the image contrast effect.

The cell image will be contaminated by random signals (also known as noise) of different intensities during a process of the acquisition, and this will have unpredictable effects on subsequent image analysis and processing. Therefore, the cell image is normalized, and gamma corrected, these reduce the influence of noise, thereby improving an accuracy of the stem cell detection model to detect the cell image.

The input module 203 inputs the plurality of sub-images into a stem cell detection model to detect to obtain a number of stem cells in each sub-image.

The plurality of sub-images is input into the stem cell detection model to obtain the number of stem cells in each of the plurality of sub-images. An accuracy of the number of stem cells detected by the stem cell detection model is relatively high. In other embodiments, a plurality of threads can be created, one stein cell detection model is arranged in each thread, so the number of the stem cell detection models is equal to the number of the plurality of threads. One stem cell detection model is used to detect one sub-image. In this way, the sub-images can be detected in parallel, thereby improving an efficiency of detecting the number of stein cells in the cell image.

In some embodiments, when each sub-image is normalized and corrected, the input module 203 inputting the plurality of sub-images into a stem cell detection model to detect to obtain a number of stem cells in each sub-image includes inputting each corrected image into the stem cell detection model to detect to obtain a number of stem cells in the corresponding sub-image.

When one corrected image is inputted into the stem cell detection model, the stem cell detection model detects a number of stem cells in the one corrected image. One corrected image is corresponding to one sub-image. The number of stem cells in the corrected image is the number of stem cells shown in the corresponding sub-image.

In some embodiments, after inputting the plurality of sub-images into the stem cell detection model, the device further includes a determination module and a generation module. The determination module configured to determine whether the number of stem cells in each sub-image is greater than a preset second threshold. When it is determined that the number of stem cells in any one sub-image is greater than the preset second threshold, the generation module configured to generate an alarm and send the alarm to a preset terminal device.

For each sub-image, it is determined whether the number of stein cells in the sub-image is greater than the preset second threshold. If the number of stem cells in any one sub-image is less than or equal to the preset second threshold, it indicates that the number of stem cells in the sub-image is normal. If the number of stem cells in any one sub-image is greater than the preset second threshold, this shows that there are too many stem cells in the sub-image, and then an alarm is generated to draw the attention of staff.

The determination module 204 determines a position of each sub-image in the cell image.

The position of each sub-image in the cell image is determined. The position of the sub-image in the cell image can be represented by pre-set characters. For example, in an order from left to right and from top to bottom, like a subscript of a two-dimensional array. A numeric value "11" represents a position of a sub-image in a first row and a first column in the cell image. A numeric value "12" represents a position of a sub-image in a first row and a second column in the cell image. Numeric values "21", 22, and 23 indicate the positions of three adjacent sub-images, from left to right, in a second row in the cell image.

The determination module 204 outputs a distribution of the stein cells in the cell image, according to the number of stem cells in each sub-image and the position of each sub-image in the cell image.

The distribution of the stem cells in the cell image represents a number of stem cells at each position in the cell image.

In some embodiments, after the determination module 204 outputs a distribution of the stem cells in the cell image, the device further includes a receiving module, configured to receive an instruction to analyze for stem cells in a designated area in the cell image. The determination module 204 acquires a target sub-image corresponding to the designated area from the plurality of sub-images. The number of stem cells in the target sub-image is determined as a target number of stein cells in the designated area; and whether the target number is determined to be greater than a preset first threshold. Information that the stem cells are not aggregated in the designated area in the cell image is displayed, when the target number is less than or equal to the preset first threshold.

In the above embodiment, when the target number is less than or equal to the preset first threshold, it indicates that there is no accumulation of stein cells in the designated area in the cell image.

In other embodiments, when it is determined that the target number is less than or equal to the preset first threshold, this information, but no other information, may be displayed on the cell image.

In some embodiments, when the target number is greater than the preset first threshold, the device further includes an output module, configured to display information that the stem cells are aggregated in the designated area in the cell image.

In the above embodiment, when the target number is greater than the preset first threshold, it indicates that there is accumulation of stem cells in the designated area in the cell image. When it is determined that there is accumulation of stem cells in the designated area in the cell image, the information that the stem cells are aggregated can be displayed in the designated area in the cell image, it may be displayed in a form of text on the designated area in the image.

By displaying information that the stem cells are aggregated in the designated area in the cell image, assessing the number of stem cells in certain areas in the image can be done intuitively.

In some embodiments, after outputting a distribution of the stein cells in the cell image and in response to an instruction for calculating a total number of stem cells in the cell image, the device further includes a first calculation module, configured to calculate the number of stem cells in each sub-image and obtain a total number of stem cells in the cell image and outputting the total number of stem cells in the cell image.

The total number of stem cells in the cell image can be obtained by adding up the number of stem cells in all the sub-images.

In the device of determining a distribution of stem cells in a cell image provided by the embodiments of the present disclosure, a cell image is segmented into a plurality of smaller sub-images, and the smaller sub-images are analyzed in parallel through a stem cell detection model to obtain the number of stein cells in each sub-image, thereby obtaining the number of stem cells in the cell image. According to the number of stem cells in each sub-image and the position of each sub-image in the cell image, the distribution of stem cells in the cell image can be determined. The efficiency of determining the distribution of stem cells in the cell image is improved, and at the same time, the accuracy is also improved.

The embodiment also provides a non-transitory readable storage medium having computer-readable instructions stored therein. The computer-readable instructions are executed by a processor to implement the steps in the above-mentioned image processing method, such as in steps in blocks S11-S15 shown in FIG. 1:

In block S11, acquiring a cell image;
In block S12, segmenting the cell image and obtaining a plurality of sub-images;
In block S13, inputting the plurality of sub-images into a stein cell detection model to detect to obtain a number of stem cells in each sub-image;
In block S14, determining a position of each sub-image in the cell image;
In block S15, outputting a distribution of the stem cells in the cell image, according to the number of stem cells in each sub-image and the position of each sub-image in the cell image.

The computer-readable instructions are executed by the processor to realize the functions of each module/unit in the above-mentioned device embodiments, such as the modules 201-204 in FIG. 2:

The acquisition module 201 acquires a cell image;
The segmentation module 202 segments the cell image and obtaining a plurality of sub-images;

The input module 203 inputs the plurality of sub-images into a stem cell detection model to detect to obtain a number of stem cells in each sub-image;

The determination module 204 determines a position of each sub-image in the cell image;

The determination module 204 outputs a distribution of the stem cells in the cell image, according to the number of stem cells in each sub-image and the position of each sub-image in the cell image.

Figure 3:
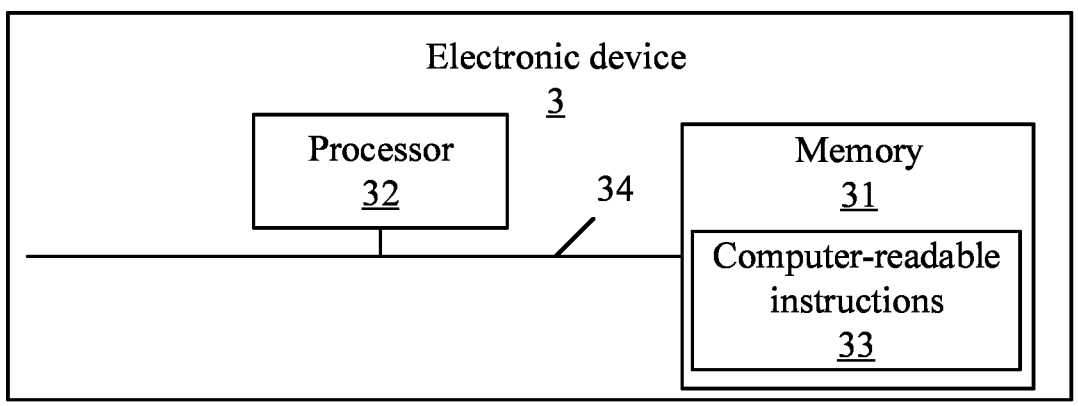
FIG. 3 shows a schematic structural diagram of an electronic device provided in an embodiment of the present disclosure.

FIG. 3 is a schematic structural diagram of an electronic device provided in an embodiment of the present disclosure. The electronic device 3 may include: a memory 31, at least one processor 32, computer-readable instructions 33 stored in the memory 31 and executable on the at least one processor 32, for example, programs of determining a distribution of stem cells in a cell image, and at least one communication bus 34. The processor 32 executes the computer-readable instructions 33 to implement the steps in the embodiment of the method of determining a distribution of stem cells in a cell image, such as in steps in block S11-S15 shown in FIG. 1. Alternatively, the processor 32 executes the computer-readable instructions 33 to implement the functions of the modules/units in the foregoing device embodiments, such as the modules 201-204 in FIG. 2.

For example, the computer-readable instructions 33 can be divided into one or more modules/units, and the one or more modules/units are stored in the memory 31 and executed by the at least one processor 32. The one or more modules/units can be a series of computer-readable instruction segments capable of performing specific functions, and the instruction segments are used to describe execution processes of the computer-readable instructions 33 in the electronic device 3. For example, the computer-readable instruction can be divided into the acquisition module 201, the segmentation module 202, the input module 203, and the determination module 204 as in FIG. 2.

The electronic device 3 can be an electronic device such as a desktop computer, a notebook, a palmtop computer, and a cloud server. Those skilled in the art will understand that the schematic diagram 3 is only an example of the electronic device 3 and does not constitute a limitation on the electronic device 3. Another electronic device 3 may include more or fewer components than shown in the figures or may combine some components or have different components. For example, the electronic device 3 may further include an input/output device, a network access device, a bus, and the like.

The at least one processor 32 can be a central processing unit (CPU), or can be another general-purpose processor, digital signal processor (DSPs), application-specific integrated circuit (ASIC), Field-Programmable Gate Array (FPGA), another programmable logic device, discrete gate, transistor logic device, or discrete hardware component, etc. The processor 32 can be a microprocessor or any conventional processor. The processor 32 is a control center of the electronic device 3 and connects various parts of the entire electronic device 3 by using various interfaces and lines.

The memory 31 can be configured to store the computer-readable instructions 33 and/or modules/units. The processor 32 may run or execute the computer-readable instructions 33 and/or modules/units stored in the memory 31 and may call up data stored in the memory 31 to implement various functions of the electronic device 3. The memory 31 mainly includes a storage program area and a storage data area. The storage program area may store an operating system, and an application program required for at least one function (such as a sound playback function, an image playback function, etc.), etc. The storage data area may store data (such as audio data, phone book data, etc.) created according to the use of the electronic device 3. In addition, the memory 31 may include a high-speed random access memory, and may also include a non-transitory storage medium, such as a hard disk, an internal memory, a plug-in hard disk, a smart media card (SMC), a secure digital (SD) Card, a flashcard, at least one disk storage device, a flash memory device, or another non-transitory solid-state storage device.

When the modules/units integrated into the electronic device 3 are implemented in the form of software functional units having been sold or used as independent products, they can be stored in a non-transitory readable storage medium. Based on this understanding, all or part of the processes in the methods of the above embodiments implemented by the present disclosure can also be completed by related hardware instructed by computer-readable instructions 33. The computer-readable instructions 33 can be stored in a non-transitory readable storage medium. The computer-readable instructions 33, when executed by the processor, may implement the steps of the foregoing method embodiments. The computer-readable instructions 33 include computer-readable instruction codes, and the computer-readable instruction codes can be in a source code form, an object code form, an executable file, or some intermediate form. The non-transitory readable storage medium can include any entity or device capable of carrying the computer-readable instruction code, such as a recording medium, a U disk, a mobile hard disk, a magnetic disk, an optical disk, a computer memory, or a read-only memory (ROM).

In the several embodiments provided in the preset application, the disclosed electronic device and method can be implemented in other ways. For example, the embodiments of the devices described above are merely illustrative. For example, divisions of the units are only logical function divisions, and there can be other manners of division in actual implementation.

In addition, each functional unit in each embodiment of the present disclosure can be integrated into one processing unit, or can be physically present separately in each unit or two or more units can be integrated into one unit. The above modules can be implemented in a form of hardware or in a form of a software functional unit.

The present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims. All changes and variations in the meaning and scope of equivalent elements are included in the present disclosure. Any reference sign in the claims should not be construed as limiting the claim. Furthermore, the word "comprising" does not exclude other units nor does the singular exclude the plural. A plurality of units or devices stated in the system claims may also be implemented by one unit or device through software or hardware. Words such as "first" and "second" are used to indicate names, but not in any particular order.

Finally, the above embodiments are only used to illustrate technical solutions of the present disclosure and are not to be taken as restrictions on the technical solutions. Although the present disclosure has been described in detail with reference to the above embodiments, those skilled in the art should understand that the technical solutions described in one embodiment can be modified, or some of the technical features can be equivalently substituted, and that these modifications or substitutions are not to detract from the essence of the technical solutions or from the scope of the technical solutions of the embodiments of the present disclosure.

What is claimed is:

1. A method of determining a distribution of stem cells in a cell image, the method comprising:
    acquiring a cell image;
    segmenting the cell image and obtaining a plurality of sub-images;
    detecting the plurality of sub-images by using a stem cell detection model and obtaining a number of stem cells in each sub-image;
    determining a position of each sub-image in the cell image;
    outputting a distribution of the stem cells in the cell image, according to the number of stem cells in each sub-image and the position of each sub-image in the cell image;
    receiving an instruction to analyze for stem cells in a designated area in the cell image, after outputting a distribution of the stem cells in the cell image;
    acquiring a target sub-image corresponding to the designated area from the plurality of sub-images;
    determining the number of stem cells in the target sub-image as a target number of stem cells in the designated area;
    determining whether the target number is greater than a preset first threshold; and
    displaying information that the stem cells are not aggregated in the designated area in the cell image, when the target number is less than or equal to the preset first threshold.

2. The method according to claim 1, the method further comprises:
    displaying information that the stem cells are aggregated in the designated area in the cell image, when the target number is greater than the preset first threshold.

3. The method according to claim 1, wherein a process of training the stem cell detection model comprises:
    acquiring a plurality of stem cell sample images;
    extracting features of each stem cell sample image through a residual convolutional network;
    generating a plurality of first feature maps through a feature pyramid network, according to the extracted features of each stem cell sample;
    generating a plurality of candidate feature maps through a region candidate network, according to the plurality of first feature maps;
    screening the plurality of candidate feature maps according to a preset intersection ratio threshold to obtain a plurality of target feature maps;
    inputting each first feature map and the corresponding target feature map to a region of interest pooling layer and obtaining a plurality of second feature maps;
    performing a regression training on the plurality of second feature maps and a number of stem cells in each second feature map and obtaining the stem cell detection model.

4. The method according to claim 3, the method further comprising:
    normalizing each sub-image to obtain a plurality of normalized images, after segmenting the cell image and obtaining a plurality of sub-images;
    performing gamma correction on each normalized image to obtain a plurality of corrected images;
    wherein inputting the plurality of sub-images into a stem cell detection model to detect to obtain a number of stem cells in each sub-image comprises: inputting each corrected image into the stem cell detection model to detect to obtain a number of stem cells in the corresponding sub-image.

5. The method according to claim 3, the method further comprising:
    determining whether the number of stem cells in each sub-image is greater than a preset second threshold;
    when it is determined that the number of stem cells in any one sub-image is greater than the preset second threshold, generating an alarm and sending the alarm to a preset terminal device.

6. The method according to claim 3, the method further comprising:
    in response to an instruction for calculating a total number of stem cells in the cell image, calculating the number of stem cells in each sub-image and obtaining a total number of stem cells in the cell image;
    outputting the total number of stem cells in the cell image.

7. An electronic device comprising a memory and a processor, the memory stores at least one computer-readable instruction, which when executed by the processor causes the processor to:
    acquire a cell image;
    segment the cell image and obtain a plurality of sub-images;
    detect the plurality of sub-images by using a stem cell detection model and obtain a number of stem cells in each sub-image;
    determine a position of each sub-image in the cell image;
    output a distribution of the stem cells in the cell image, according to the number of stem cells in each sub-image and the position of each sub-image in the cell image;
    receive an instruction to analyze for stem cells in a designated area in the cell image, after outputting a distribution of the stem cells in the cell image;
    acquire a target sub-image corresponding to the designated area from the plurality of sub-images;
    determine the number of stem cells in the target sub-image as a target number of stem cells in the designated area;
    determine whether the target number is greater than a preset first threshold; and
    display information that the stem cells are not aggregated in the designated area in the cell image, when the target number is less than or equal to the preset first threshold.

8. The electronic device according to claim 7, wherein the processor is further caused to:
    display information that the stem cells are aggregated in the designated area in the cell image, when the target number is greater than the preset first threshold.

9. The electronic device according to claim 7, wherein the processor is further caused to:
    acquire a plurality of stem cell sample images;
    extract features of each stem cell sample image through a residual convolutional network;
    generate a plurality of first feature maps through a feature pyramid network, according to the extracted features of each stem cell sample;
    generate a plurality of candidate feature maps through a region candidate network, according to the plurality of first feature maps;

screen the plurality of candidate feature maps according to a preset intersection ratio threshold to obtain a plurality of target feature maps;
input each first feature map and the corresponding target feature map to a region of interest pooling layer and obtain a plurality of second feature maps;
perform a regression training on the plurality of second feature maps and a number of stem cells in each second feature map and obtain the stem cell detection model.

10. The electronic device according to claim 9, wherein the processor is further caused to:
normalize each sub-image to obtain a plurality of normalized images, after segmenting the cell image and obtaining a plurality of sub-images;
perform gamma correction on each normalized image to obtain a plurality of corrected images;
wherein inputting the plurality of sub-images into a stem cell detection model to detect to obtain a number of stem cells in each sub-image comprises: inputting each corrected image into the stem cell detection model to detect to obtain a number of stem cells in the corresponding sub-image.

11. The electronic device according to claim 9, wherein the processor is further caused to:
determine whether the number of stem cells in each sub-image is greater than a preset second threshold;
when it is determined that the number of stem cells in any one sub-image is greater than the preset second threshold, generate an alarm and sending the alarm to a preset terminal device.

12. The electronic device according to claim 9, wherein the processor is further caused to:
in response to an instruction for calculating a total number of stem cells in the cell image, calculate the number of stem cells in each sub-image and obtain a total number of stem cells in the cell image;
output the total number of stem cells in the cell image.

13. A non-transitory storage medium having stored thereon at least one computer-readable instructions that, when the at least one computer-readable instructions are executed by a processor to implement a method of determining a distribution of stem cells in a cell image, which comprises:
acquiring a cell image;
segmenting the cell image and obtaining a plurality of sub-images;
detecting the plurality of sub-images by using a stem cell detection model and obtaining a number of stem cells in each sub-image;
determining a position of each sub-image in the cell image;
outputting a distribution of the stem cells in the cell image, according to the number of stem cells in each sub-image and the position of each sub-image in the cell image;
receiving an instruction to analyze for stem cells in a designated area in the cell image, after outputting a distribution of the stem cells in the cell image;
acquiring a target sub-image corresponding to the designated area from the plurality of sub-images;
determining the number of stem cells in the target sub-image as a target number of stem cells in the designated area;
determining whether the target number is greater than a preset first threshold; and
displaying information that the stem cells are not aggregated in the designated area in the cell image, when the target number is less than or equal to the preset first threshold.

14. The non-transitory storage medium according to claim 13, the method further comprises:
displaying information that the stem cells are aggregated in the designated area in the cell image, when the target number is greater than the preset first threshold.

15. The non-transitory storage medium according to claim 13, wherein a process of training the stem cell detection model comprises:
acquiring a plurality of stem cell sample images;
extracting features of each stem cell sample image through a residual convolutional network;
generating a plurality of first feature maps through a feature pyramid network, according to the extracted features of each stem cell sample;
generating a plurality of candidate feature maps through a region candidate network, according to the plurality of first feature maps;
screening the plurality of candidate feature maps according to a preset intersection ratio threshold to obtain a plurality of target feature maps;
inputting each first feature map and the corresponding target feature map to a region of interest pooling layer and obtaining a plurality of second feature maps;
performing a regression training on the plurality of second feature maps and a number of stem cells in each second feature map and obtaining the stem cell detection model.

16. The non-transitory storage medium according to claim 15, the method further comprising:
normalizing each sub-image to obtain a plurality of normalized images, after segmenting the cell image and obtaining a plurality of sub-images;
performing gamma correction on each normalized image to obtain a plurality of corrected images;
wherein inputting the plurality of sub-images into a stem cell detection model to detect to obtain a number of stem cells in each sub-image comprises: inputting each corrected image into the stem cell detection model to detect to obtain a number of stem cells in the corresponding sub-image.

17. The non-transitory storage medium according to claim 15, the method further comprising:
determining whether the number of stem cells in each sub-image is greater than a preset second threshold;
when it is determined that the number of stem cells in any one sub-image is greater than the preset second threshold, generating an alarm and sending the alarm to a preset terminal device.

* * * * *